United States Patent [19]

Kinney et al.

[11] Patent Number: 4,958,023
[45] Date of Patent: Sep. 18, 1990

[54] 2-PYRIDINECARBOTHIOAMIDES, PROCESSES FOR PREPARATION THEREOF AND PHARMACEUTICAL COMPOSITIONS COMPRISING THE SAME

[75] Inventors: William A. Kinney, Langhorne, Pa.; Nancy E. Lee, Edison, N.J.

[73] Assignee: American Home Products Corporation, New York, N.Y.

[21] Appl. No.: 373,751

[22] Filed: Jun. 29, 1989

Related U.S. Application Data

[62] Division of Ser. No. 246,475, Sep. 19, 1988, Pat. No. 4,873,238.

[51] Int. Cl.$^5$ ................ C07D 213/52; C07D 295/092
[52] U.S. Cl. .................... 544/58.6; 544/111; 544/365; 546/193; 546/340
[58] Field of Search ............ 546/339, 193, 340; 548/336; 544/58.6, 111, 365; 568/812

[56] References Cited

U.S. PATENT DOCUMENTS

| | | | |
|---|---|---|---|
| 2,765,346 | 10/1956 | Paul et al. | 568/814 |
| 2,838,509 | 6/1958 | Cusic | 544/58.6 |
| 3,192,207 | 6/1985 | Lumsford et al. | 546/193 |
| 3,953,434 | 4/1976 | Hauck et al. | 546/339 |
| 4,504,484 | 3/1985 | Spatz | 514/357 |
| 4,564,613 | 1/1986 | Boltze et al. | 544/58.6 |
| 4,709,059 | 11/1987 | Dirlikov et al. | 549/453 |

FOREIGN PATENT DOCUMENTS 952635 11/1956 Fed. Rep. of Germany .
3339644 3/1960 Fed. Rep. of Germany .

OTHER PUBLICATIONS

Tam, et al. Chem. Pharm. Bull. 30(10) 3530-3543 (1982).
Morrison and Boyd, Organic Chemistry, 3rd Ed. (Boston, Allyn and Bacon 1973) pp. 756, 757 and 738.
Morrison and Boyd, Organic Chemistry (Boston, Allen and Bacon, 1979) p. 742.
E. A. Popova et al, Deposited Doc. 1981 SPSTL 586 Khp-D81 (CA 98:50236a).

*Primary Examiner*—Mukund J. Shah
*Assistant Examiner*—E. C. Ward
*Attorney, Agent, or Firm*—Walter Patton

[57] ABSTRACT

There are provided gastric antiulcer and cytoprotective substituted N-phenyl-2-pyridinecarbothioamides. The process for their production and formulation is disclosed.

1 Claim, No Drawings

2-PYRIDINECARBOTHIOAMIDES, PROCESSES FOR PREPARATION THEREOF AND PHARMACEUTICAL COMPOSITIONS COMPRISING THE SAME

This is a divisional application of copending application U.S. Ser. No. 07/246,475, filed Sept. 19, 1988 now U.S. Pat. No. 4,873,238.

BACKGROUND OF THE INVENTION

The present invention relates to novel 2-pyridinecarbothioamides. More particularly, it relates to novel 2-pyridinecarbothioamides which have inhibitory activity on ulcers, to processes for preparation thereof, to pharmaceutical compositions comprising the same, and to the method of using the same therapeutically in the treatment of ulcers in human beings and animals.

The compounds of the present invention have the following formula:

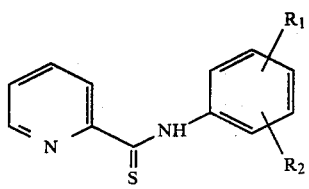

wherein,

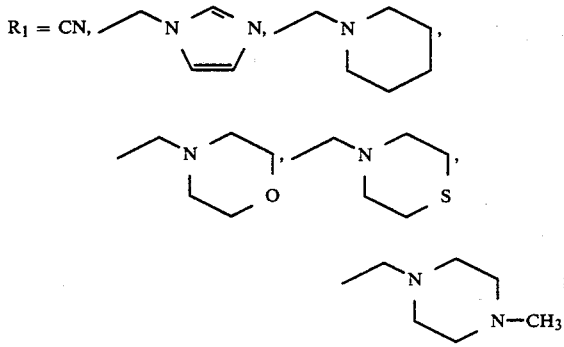

$R_2 =$ H or F

The closest prior art is W. A. Kinney et al, Canadian patent application, Serial No. 528,269, filed Jan. 27, 1987; B. Emmert and M. Groll, German Patent No. 952,635 (1956), and E. A. Popova et al, Deposited Doc. 1981, SPSTL 586 Khp-D81. They disclose a number of 2-pyridinecarbothioamides as cytoprotective agents, as intermediates in the preparation of therapeutics and as bactericidal agents, respectively. However, the compounds of the present invention are not exemplified in the numerous examples contained in the above-mentioned references.

Although the mechanism of cytoprotection is not clearly defined yet, there is a suggestion that it may be partially mediated through the release of gastric mucosal prostaglandins, (Hollander et al, Gastroenterology 86: 1114, 1984; and Tarnawski et al, Gastroenterology 86: 1276, 1984). Szelenyi et al, (Gastroenterology 88: 1604, 1985) has suggested non-prostaglandin mediated mechanisms for cytoprotection.

Activity in the ethanol-induced ulcer model is an indication of cytoprotection, regardless of the antisecretory characteristics of the drug. Antisecretory agents, such as the $H_2$ receptor antagonist cimetidine and the anticholinergic agent propantheline bromide, do not protect in this model. See Robert et al., Scand. J. Gastroenterol. 19 (Suppl. 101): 69–72, 1984.

The compounds of this invention have been found to possess effective gastric and duodenal cytoprotective properties. These properties, along with a relatively low order of toxicity, render these compounds valuable agents for treating ulcers in humans and animals.

SUMMARY OF THE INVENTION

Accordingly, one object of this invention is to provide novel 2-pyridinecarbothioamides which are useful as a medicine for ulcers.

Another object of this invention is to provide processes for the preparation of said 2-pyridinecarbothioamides.

A further object of this invention is to provide pharmaceutical compositions comprising, as an active ingredient, said 2-pyridinecarbothioamides.

A still further object of this invention is to provide a method of using said 2-pyridinecarbothioamides in the treatment of ulcers in human beings and animals.

DETAILS OF THE INVENTION

We have demonstrated that the 2-pyridinecarbothioamides of the present invention inhibit ethanol-induced ulcers in rats. The activity of said compounds in this test suggests, therefore, that they possess digestive tract cytoprotective properties. Because of their cytoprotective nature they may be used to treat or prevent disease states such as regional ileitis, Crohn's disease, erosive gastritis, erosive esophagitis, inflammatory bowel disease and ethanol-induced hemorrhagic erosions.

For therapeutic purposes, the compounds according to the present invention can be used in pharmaceutical preparations containing said compounds as an active ingredient, in admixture with a pharmaceutically acceptable carrier such as an organic or inorganic solid or liquid excipient suitable for oral or parenteral administration. The pharmaceutical preparations may be capsules, tablets, dragees, solutions, suspensions, emulsions, and the like. If desired, there may be included in the above preparations auxiliary substances, stabilizing agents, wetting or emulsifying agents, buffers, and other commonly used additives.

While the dosage of the compounds will vary depending upon the age and condition of the patient, an average single dose of about 1 to 100 mg/kg of the compounds according to the present invention may be effective for treating ulcers. In general, amounts between 1 to 10 mg/kg may be administered per day.

The 2-pyridinecarbothioamides of this invention are novel and can be represented by the following general formula (I):

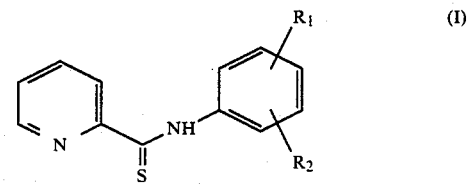

wherein,

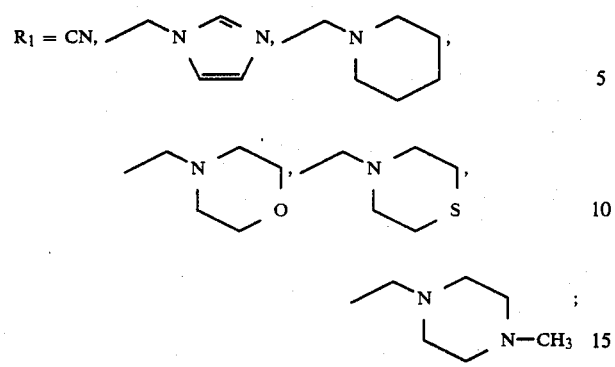

$R_2$=H or F, and the pharmaceutically acceptable salts thereof.

The preferred compounds of the present invention are:

Example:
1. N-[4-fluoro-3-[(1H-imidazol-1-yl)methyl]phenyl]-2-pyridinecarbothioamide;
2. N-[4-fluoro-3-(piperidinylmethyl)phenyl]-2-pyridinecarbothioamide;
3. N-(4-cyanophenyl)-2-pyridinecarbothioamide;
4. N-(3-cyanophenyl)-2-pyridinecarbothioamide;
5. N-[3-[(1H-imidazol-1-yl)methyl]phenyl]-2-pyridinecarbothioamide;
6. N-[3-(piperidinylmethyl)phenyl]-2-pyridinecarbothioamide;
7. N-[4-(piperidinlymethyl)phenyl]-2-pyridinecarbothioamide;
8. N-[3-[(4-morpholinyl)methyl]phenyl]-2-pyridinecarbothioamide;
9. N-[3-[(4-thiomorpholinyl)methyl]phenyl]-2-pyridinecarbothioamide;
10. N-[3-[(4-methyl-1-piperazinyl)methyl]phenyl]-2-pyridinecarbothioamide and the pharmaceutically acceptable salts thereof.

The compounds of this invention are capable of forming acid addition salts with therapeutically acceptable acids. The acid addition salts are prepared by reacting the base form of the appropriate compound (I) with one or more equivalents, preferably with an excess, of the appropriate acid in an organic solvent, for example, diethyl ether or an ethanol diethyl ether mixture.

These salts, when administered to a mammal, possess the same or improved pharmacological activities as the corresponding bases. For many purposes it is preferable to administer the salts rather than the basic compounds. Suitable acids to form these salts include the common mineral acids, e.g. hydrohalic, sulfuric, or phosphoric acid; the organic acids, e.g. ascorbic, citric, lactic, aspartic, or tartaric acid. The preferred salt is the hydrochloride salt. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

According to this invention, the compounds (I) can be prepared by the following general process:

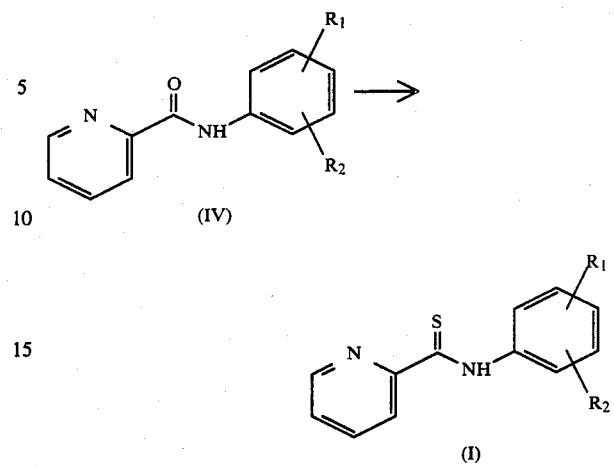

wherein $R_1$ and $R_2$ are each as defined above.

The specific processes for preparing the object compounds (I) are explained here in detail below.

Process A

The compounds (I) can be prepared by reacting a compound (IV) with a thiation agent (e.g. $P_4S_{10}$ or Lawesson's Reagent [2,4-bis(4-methoxyphenyl)-1,3-dithia-2,4-diphosphetane-2,4-disulfide] Tetrahedron Lett., 21, 4061 (1980).

This reaction is usually carried out in benzene, toluene, xylene or pyridine or any other solvent which does not adversely affect the reaction. The reaction is usually carried out under heating.

Process B

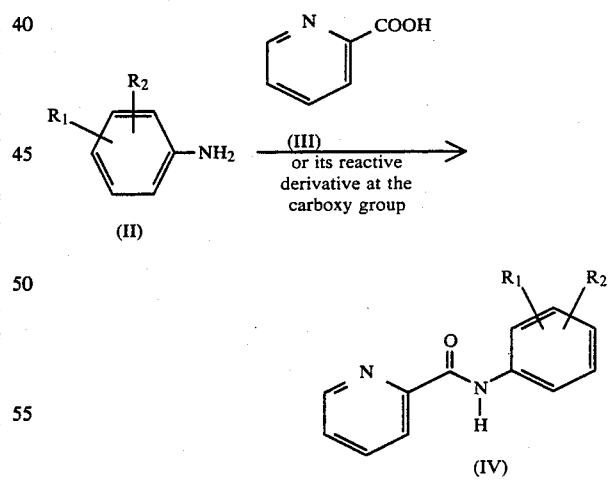

The compound (IV) can be prepared by reacting a compound (II) with a compound (III) or its reactive derivative at the carboxy group, wherein

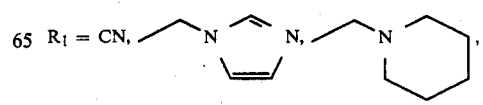

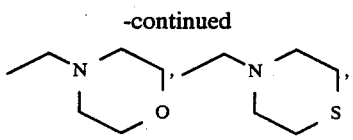

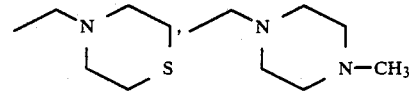

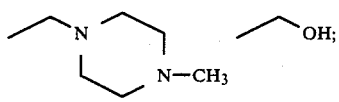

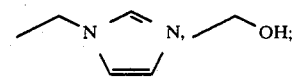

$R_2 = H$ or F.

Suitable reactive derivatives at the carboxy group of the compound (III) may include an acid halide, an acid anhydride, an ester, an activated amide, an activated ester and the like.

Suitable examples of such reactive derivatives may be an ester, such as lower alkyl ester (e.g. methyl ester, ethyl ester, propyl ester, or hexyl ester), acid chloride, an acid azide, a mixed acid anhydride with an acid, such as substituted phosphoric acid (e.g. dialkylphosphoric acid, or phenylphosphoric acid), aliphatic carboxylic acid (e.g. pivalic acid, acetic acid, or trichloroacetic acid) or the like, a symmetrical acid anhydride, an activated amide with imidazole, triazole, or dimethylpyrazole, an activated ester with N-hydroxysuccinimide, N-hydroxyphthalimide or 1-hydroxy-6-chlorobenzotriazole, and the like.

When a compound (III) is used in a free acid form, the reaction is preferably carried out in the presence of a conventional condensing agent such as N,N'-dicyclohexylcarbodiimide, N,N'-carbonyldiimidazole, N-cyclohexyl-N'-morpholinoethylcarbodiimide, N-ethyl-N'-(3-dimethylaminopropyl)carbodiimide, thionyl chloride, phosphorus oxychloride, phosphorus oxybromide, oxalyl chloride, lower alkoxycarbonyl halide (e.g. ethyl chloroformate, or isobutyl chloroformate), 1-(p-chlorobenzenesulfonyloxy)-6-chloro-1H-benzotriazole, or the like.

The reaction is usually carried out in a conventional solvent such as dioxane, chloroform, methylene chloride, ethylene chloride, tetrahydrofuran, ethyl acetate, N,N-dimethylformamide, pyridine, or any other organic solvent which does not adversely influence the reaction.

The reaction temperature is not critical, and the reaction can be carried out under cooling, at ambient temperature, or under warming or heating.

Process C

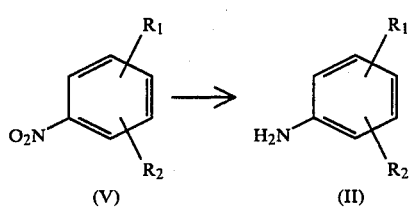

The compounds (II), wherein

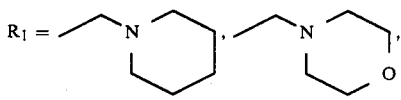

$R_2 = H$ or F can be prepared by reduction of the aromatic nitro compound (V) with hydrogen and a catalyst, stannous chloride dihydrate, zinc in hydrochloric acid, tin in hydrochloric acid, or iron in hydrochloric acid.

The reaction can be carried out in the presence of a conventional solvent, such as methanol, ethanol, acetic acid, ethyl acetate, or any other organic solvent that does not adversely influence the reaction.

Process D

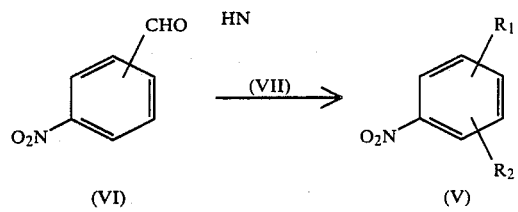

The compounds (V), wherein

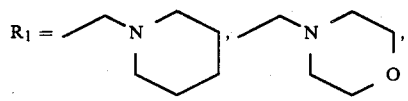

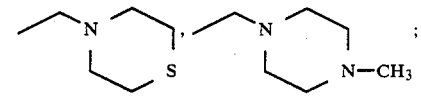

$R_2 = H$ can be prepared by reacting the aldehyde (VI) with the appropriate heterocycle (VII) in the presence of a mild reducing agent, such as zinc modified cyanoborohydride [Kim et al., J. Org. Chem., 50, 1927 (1985)], sodium cyanoborohydride, or sodium borohydride.

The reaction can be carried out in the presence of a conventional solvent, such as methanol, ethanol, acetic acid, ethyl acetate, ether, or any other organic solvent that does not adversely influence the reaction.

Process E

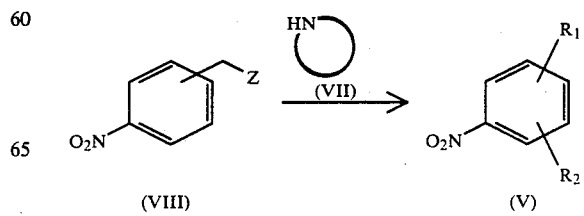

The compounds (V), wherein

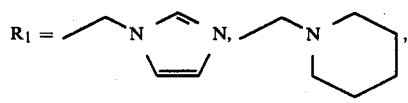

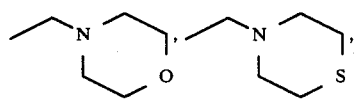

$R_2 = H$ can be prepared [Baggaley et al., J. Med. Chem 18, 833 (1975)] by reacting the appropriate heterocycle (VII) or a corresponding reactive salt of (VII) with the benzylic halide (VIII), wherein Z=bromide, chloride, or iodide.

Suitable reactive salts of (VII) would be the sodium or potassium salts, which can be prepared by reacting (VII) with an inorganic base, such as alkali metal hydride (e.g. sodium hydride, or potassium hydride, and the like).

This reaction can be carried out in the presence of conventional solvents, such as N,N-dimethylformamide, an aromatic hydrocarbon (e.g. benzene, toluene, or xylene, and the like), or any other organic solvent that does not adversely influence the reaction.

The reaction can be carried out at ambient temperature, under heating, or under cooling.

Process F

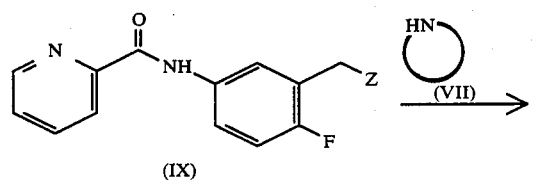

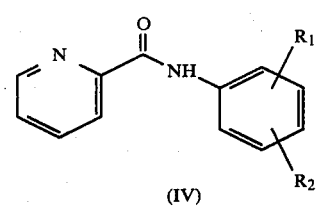

The compounds (IV), wherein

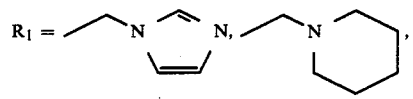

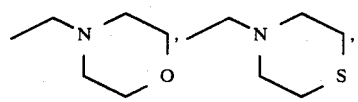

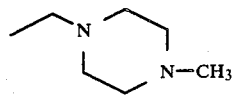

$R_2 = F$ are prepared by reacting the appropriate heterocycle (VII) or a corresponding reactive salt of (VII) with the benzylic halide (IX), wherein Z=bromide, chloride, or iodide.

Suitable reactive salts of (VII) would be the sodium or potassium salts, which can be prepared by reacting (VII) with an inorganic base, such as alkali metal hydride (e.g. sodium hydride, or potassium hydride, and the like).

This reaction can be carried out in the presence of conventional solvents, such as N,N-dimethylformamide, an aromatic hydrocarbon (e.g. benzene, toluene, or xylene, and the like), or any other organic solvent that does not adversely influence the reaction.

The reaction can be carried out in ambient temperature, under heating, or under cooling.

Process G

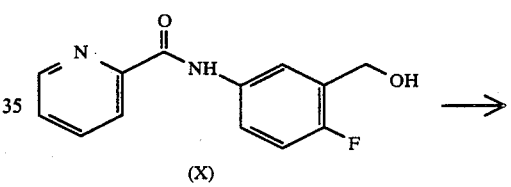

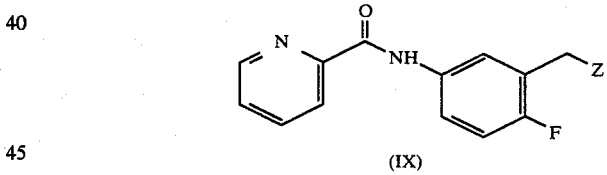

The compounds (IX) wherein Z=bromide, chloride, or iodide are prepared by reacting (X) with a halogenating reagent.

Suitable halogenating reagents are carbon tetrabromide and triphenylphosphine [Hooz et al. Can. J. Chem. 46, 86 (1968)], phosphorus tribromide, hydrogen bromide, thionyl chloride, phosphorus pentachloride, phosphorus trichloride, phosphorus oxychloride, and hydrogen iodide.

This reaction can be carried out in the presence of conventional solvents, such as tetrahydrofuran, an aromatic hydrocarbon (e.g. benzene, toluene, or xylene, and the like), a halogenated solvent (e.g. dichloromethane, chloroform, and the like), or any other organic solvent which does not adversely influence the reaction.

The reaction can be carried out at ambient temperature, under heating, or under cooling.

Process H (XI) → (XII)

The nitro alcohol (XII), which was converted to (X) by processes C and B, was prepared from (XI) by selective reduction of the aldehyde group.

Suitable reducing agents include sodium borohydride, diborane, aluminum hydride, and diisobutylaluminum hydride.

The reaction can be carried out in the presence of a conventional solvent, such as an alcohol (e.g. methanol or ethanol, and the like), tetrahydrofuran, an aromatic hydrocarbon (e.g. benzene or toluene, and the like), or any other organic solvent that does not adversely influence the reaction.

The reaction can be carried out at ambient temperature with heating or cooling.

In order to illustrate the usefulness of the compounds of the present invention, they were subjected to the following pharmacological assays.

ETHANOL INDUCED CYTOTOXICITY IN RATS

The purpose of this assay is to evaluate the effectiveness of the compounds of the present invention in preventing the formation of gastric mucosal lesions produced by ethanol. The assay is based on A. Robert et al., Gastroenterology 77, 433–443 (1979).

Male Sprague-Dawley rats weighing between 120–150 grams were fasted for 24 hours prior to the experiment (water ad libitum). At least two hours before dosing, the animals were placed in individual cages with wire grid bottoms and denied access to water.

Drug Preparation and Administration

Ethanol was administered orally at 1 mL per animal. The compounds of the present invention were dissolved in water or suspended in water with 0.5% carboxymethylcellulose and administered orally at a dose based on an appropriate standard giving $ED_{50}$ to $ED_{75}$ response of cytoprotective activity.

Methodological Details

The rats were randomly divided into groups of equal number, ordinarily 10 to a group. The rats were weighed and the individual weights were recorded. Exactly 1 hour prior to the administration of ethanol, the screening group was treated with the compounds of the present invention and the control group with the vehicle. One hour after administering the ethanol, the animals were euthanized. The stomachs were removed, cut along the greater curvature, and cleansed of all debris with tap water. The stomachs were set aside and kept moist with saline until the lesions were scored.

Sample Analysis

Macroscopic lesions on the gastric mucosa were numerically graded. The final grade assigned a stomach was the sum of all the grades.

| Grade | Description (Approximate length of lesion) |
|---|---|
| 0 | no lesion |
| 1 | 2 mm or less |
| 2 | 4 mm |
| 3 | 6 mm |

Streaks longer than 6 mm are graded in multiples of 2 mm.

Interpretation of Data:

The degree of cytotoxicity occuring in each group is represented as the mean ±SE ulcer grade.

Presentation of Results and Criteria for Activity:

The mean of each treatment group was compared to the control group and expressed as the % inhibition of lesion formation.

| Example | % Inhibition | Dose mg/kg | $ED_{50}$ mg/kg | m.p. °C. |
|---|---|---|---|---|
| 1 | — | — | 0.88 | 154–156 |
| 2 | — | — | 2.6 | 254–256 |
| 3 | — | — | 1.1 | 142–144 |
| 4 | — | — | 1.6 | 159–160 |
| 5 | — | — | 2.2 | 148–150 |
| 6 | — | — | 5.3 | 225–230 |
| 7 | — | — | 6.2 | 123–125 |
| 8 | 64 | 10 | — | 90–92 |
| 9 | 32 | 10 | — | 130–132 |
| 10 | 10 | 10 | — | 250 (dec.) |

STRESS-INDUCED GASTRIC ULCERS IN RATS

The purpose of this assay is to evaluate the effectiveness of the compounds of the present invention in preventing stress-induced ulcers.

Maile rats (280–380 g) were fasted for 18 hours (water available ad libitum) prior to use in experiments. Eight to twelve rats were used per group.

Drug Preparation and Administration:

Drug solutions or suspensions were prepared in physiological saline solution. Suspensions were prepared with the aid of 0.5% carboxymethylcellulose in physiological saline solution. Drugs were administered orally or parenterally at predetermined intervals (usually 15 to 45 minutes) prior to stress.

Methodological Details:

This test procedure is according to the method of Senay et al., Proc. Soc. Exp. Biol. Med. 124, 1221 (1967), modified to produce a more consistent ulcer incidence. After drug administration, the rats were immobilized in metallic restrainers and placed in a cold room at 4°–5° C. for 3 hours before they were euthanized. Each rat was given 20 mg of sodium taurocholate p.o. immediately before placing it in the restrainer. After euthanizing the rats, the stomachs were excised and examined. Macroscopic ulcers were subjectively assigned a grade from 1 to 3 on the basis of increasing size. The number of ulcers in each size category was determined and multiplied by the respective grade; the addition of the resultant values gave the cumulative ulcer score. The average cummulative ulcer score of each treatment group was compared to that of the control group and the percent inhibition of ulcer formation was calculated. When the responses obtained were directly proportional to the doses employed, $ED_{50}$ values were determined from the dose-response curves obtained.

| Example | Stress-Induced Ulcer $ED_{50}$mg/kg |
|---|---|
| 3 | 1.7 |
| 5 | 1.9 |
| 6 | 4.6 |

The following preparations and examples are given for the purpose of further illustrating the present invention.

EXAMPLE 1

N-[4-Fluoro-3-[(1H-imidazol-1-yl)methyl]phenyl]-2-pyridinecarbothioamide

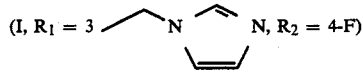

(I, $R_1 = 3$-    , $R_2 = 4$-F)

Step 1: Preparation of 3-Hydroxymethyl-4-fluoroaniline

Sodium borohydride (15.0 g, 0.397 mol) was added portionwise to a 0° C. solution of 2-fluoro-5-nitrobenzaldehyde (82.4 g, 0.487 mol) in anhydrous methanol (1 L). The reaction mixture was stirred at 0° C. for 0.5 hours and was quenched by adding 1N hydrochloric acid solution (500 mL), which resulted in a pH range of between 4 and 5. The product, which precipitated out when methanol was removed, was collected by filtration. To obtain additional product, the filtrate was extracted with ether (4×500 mL). The ether layer was washed with brine and dried to give crude material which was combined with the other material and recrystallized from ethyl acetate in petroleum ether to give 1-fluoro-2-hydroxymethyl-4-nitrobenzene (69.4 g, 0.406 mol, 83%, mp 50°-53° C.). This material was dissolved in ethyl acetate (1 L) and treated with stannous chloride dihydrate (451 g, 1.99 mol) at reflux temperature for 24 hours. The reaction mixture was poured into ice water (1.5 L), basified using 2.5N sodium hydroxide solution to pH 9, and extracted with ethyl acetate (4×1 L), which was washed with brine and dried. Removal of ethyl acetate gave 3-hydroxymethyl-4-fluoroniline (34.2 g, 60%, mp 80°-84° C.; Tani et al., Chem. Pharm. Bull. 30, 3530, 1982: mp 95°-98° C.).

$^1$H NMR (DMSO, 400 MHz): δ6.78(d of d, J=10 and 9 Hz, 1H), 6.67 (d of d, J=6 and 3 Hz, 1H), 6.41(m, 1 H), 5.11(t, J=6 Hz, OH), 4.97(br s, NH$_2$), 4.43(d, J=6 Hz, 2H).

IR (KBr, cm$^{-1}$): 3360, 1250, 1040.

MS (m/z): 141(M+, 100), 124(43), 120(47), 112(57), 92(45), 83(32), 65(29).

Step 2: Praparation of N-(4-Fluoro-3-hydroxymethyphenyl)-2-pyridinecarboxamide 3-Hydroxymethyl-4-fluoroaniline (34.2 g, 243 mmol) was dissolved in dichloromethane (600 mL) under anhydrous conditions and cooled to 0° C. Triethylamine (120 mL, 0.861 mol) was added, followed by a solution of picolinic acid chloride hydrochloride (86.0 g, 0.483 mol) in methylene chloride (300 mL). The reaction mixture was stirred at 0° C. for 0.5 hours and at room temperature for 1 hour, and poured into ice water (2 L). The resulting mixture was basified with 1N sodium hydroxide solution, extracted with methylene chloride (3×800 mL), washed with brine, and dried over magnesium sulfate to give a brown oil, which was purified by flash chromatography (6 in diameter column, elution with 25% ethyl acetate in petroleum ether) to give the title compound (10.0 g, 18%, mp 99°-122° C.) as the first compound of the column, followed by 2-pyridinecarboxylic acid [[2-fluoro-4-[[(2-pyridinyl)oxomethyl]-amino]phenyl]methyl] ester (46.5 g, 52%, mp 116°-118° C.). Additional title compound can be obtained by treating the ester (25.0 g, 71 mmol) with potassium carbonate (19.8 g, 143 mmol) in water (20 mL), methanol (200 mL), and tetrahydrofuran (200 mL). The mixture was left for 2 days and then concentrated in vacuo. The residue was partitioned between ethyl acetate (500 mL) and water (500 ml) and the aqueous layer was extracted again with ethyl acetate (2×200 mL). The organic layer was washed with 2.5N sodium hydroxide solution (500 mL) and brine (500 mL), dried, and concentrated to afford more N-(4-fluoro-3-hydroxymethylphenyl)-2-pyridinecarboxamide (15 g, 90%).

$^1$H NMR (CDCL$_3$, 400 MHz): δ10.02(br s, NH), 8.57(d, J=5Hz, 1H), 8.25(d, J=8 Hz, 1H), 7.88(t of d, J=8 and 2 Hz, 1H), 7.84-7.80(m, 1H), 7.75(d of d, J=6 and 3 Hz, 1H), 7.48-7.45(m, 1H), 7.08 (t, J=9 Hz, 1H), 5.11 (s, 2H)

IR(KBr, cm$^{-1}$): 3400, 1200, 1000

MS (m/z): 246 (M+, 46), 106(36), 79(100), 78(92), 69(33).

Step 3: Preparation of N-[3-(Bromomethyl)-4-fluorophenyl]-2-pyridinecarboxamide Carbon tetrabromide (39.4 g, 118 mmol)and triphenylphosphine (33.0 g, 118 mmol) were added to a 0° C. solution of the above alcohol (22.9 g, 98 mmol) in anhydrous tetrahydrofuran (350 mL). The reaction mixture was stirred for two hours, warmed to room temperature, and left overnight. The white precipitate was removed by filtration and the filtrate was preadsorbed onto silica gel and submitted to flash chromatography (6 in diameter column, elution with 10% ethyl acetate in petroleum ether) to give the title compound (20.6 g, 72%, mp 137°-138° C.).

$^1$H NMR (CDCl$_3$, 400 MHz): δ10.03(br s, NH), 8.61(d, J=5 Hz, 1H), 8.28(d, J=8 Hz, 1H), 7.92(m, 2H), 7.68(m, 1H), 7.49(m, 1H), 7.08(t, J=9 Hz, 1H), 4.53(s, 2H).

IR (KBr, cm$^1$): 3280, 1680, 1230.

MS (m/z): 310(M+, 8), 308(M+8), 230(29), 229(100), 106(39), 96(26), 79(78), 78(99).

Step 4: Preparation of N-[4-Fluoro-3-[(1H-imidazol-1-yl)methyl]-2-pyridinecarbothioamide.

The sodium salt of imidazole (4.0 g, 44.8 mmol) was introduced to a solution of N-[3-(bromomethyl)-4-fluorophenyl]-2-pyridinecarboxamide (10.11 g, 34.5 mmol) in anhydrous dimethylformamide (200 mL). The reaction mixture was stirred at room temperature for 2 hours, poured into water (1.2 L), extracted with ethyl acetate (3×500 mL), washed with brine, dried over magnesium sulfate, and evaporated. The crude amide was recrystallized from methanol in ethyl acetate to give a pure off-white solid (6.4 g, 22 mmol, 63%, mp 115°–117° C.). The thioamide was prepared by treating the amide in anhydrous pyridine (200 mL) with phosphorus pentasulfide (4.8 g, 11 mmol) at reflux temperature for 4 hours. The reaction mixture was poured into ice water (1 L), basified with 1N sodium hydroxide solution, extracted with ethyl acetate (3×700 mL), washed with brine, and dried. The ethyl acetate layer was preabsorbed onto silica gel and the residue was purified by flash chromatography [4 in diameter column, elution with 30% (90:5:2.5 dichloromethane: methanol:ammonium hydroxide) in dichloromethane] to yield the title compound (2.7 g, 39%, mp 154°–156° C.).

$^1$H NMR (CDCl$_3$, 400 MHz): δ11.97 (br s, NH), 8.75 (d, J=8 Hz, 1H), 8.54 (d, J=5 Hz, 1H), 8.01(m, 1H), 7.89(t of d, J=8 and 2 Hz, 1H), 7.81 (d of d, J=7 and 2 Hz, 1H), 7.62 (s, 1H),7.48 (m, 1H), 7.19 (t, J=9 Hz, 1H), 7.10 (s, 1H), 7.00 (s, 1H), 5.22 (s, 2H).

IR (KBr, cm$^{-1}$): 3400, 1500.

MS (m/z): 312 (M+, 8), 244 (60), 122 (36), 108 (46), 107 (39), 78 (79), 69(100)

Anal. Calcd. for C$_{16}$h$_{13}$FN$_4$S: C, 61.52; H, 4.19; N, 17.93 Found: C, 61.20; H, 4.29; N, 17.64.

EXAMPLE 2

N-[4-Fluoro-3-(piperidinylmethyl)phenyl]-2-pyridinecarbothioamide Hydrochloride

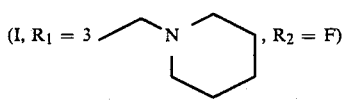

(I, R$_1$ = 3-..., R$_2$ = F)

To a solution of N-[4-fluoro-3-(bromomethyl)-phenyl]-2-pyridinecarboxamide (4.9 g, 17 mmol) in anhydrous toluene (150 mL), was introduced piperidine (3.4 mL, 33 mmol). The reaction mixture was refluxed for 1 hour, cooled, and diluted with ethyl acetate (400 mL). The organic layer washed with 1N sodium hydroxide solution (2 ×500 mL) and brine, dried, and concentrated to give a light brown oil (5.2 g, 17 mmol, 99%). The crude oil was dissolved in anhydrous pyridine (150 mL) and treated with phosphorus pentasulfide (3.7 g, 8.3 mmol) at reflux temperature for 3 hours. The reaction mixture was poured into ice water (1 L), basified with 1N sodium hydroxide solution, and extracted with ethyl acetate (3×700 mL). The organic layers were washed with brine, dried, and preabsorbed onto silica gel. Flash chromatography (4 in diameter column, elution with 5% methanol in dichloromethane) of the crude residue gave the pure thioamide as an oil. The hydrochloride salt was prepared by dissolving the thioamide in ether and adding hydrogen chloride saturated ether. The title compound was collected and recrystallized from methanol in acetone to afford a yellow solid (1.23 g, 20%, mp 254°–256° C.).

$^1$H NMR (DMSO, 400 MHz): δ12.39 (br s, NH), 10.50 (br s, NH), 8.68 (d, J=5 Hz, 1 H), 8.53 (d, J=8 Hz, 1H), 8.15 (d of d, J=7 and 2 Hz, 1H), 8.05 (t of d, J=8 and 2 Hz, 1H), 8.01 (m, 1H), 7.68 (m, 1H), 7.42 (t, J=9 Hz, 1H), 4.32 (d, J=4 Hz, 2H), 3.40–3.33 (m, 2H), 2.94–2.90 (m, 2H), 1.77–1.68 (m, 5H), 1.35 (m, 1H), IR (KBr, cm$^{-1}$): 3450, 2500, 1500.

MS (m/z): 329 (M+, 39), 246 (16), 244(15), 212(61), 207(100), 122(22), 108(34), 84(38), 78(20).

Anal. Calcd. for C$_{18}$H$_{21}$ClFN$_3$S: C, 59.09; H, 5.75; N, 11.49 Found: C, 59.08; H, 5.51; N, 11.49.

EXAMPLE 3

N-(4-Cyanophenyl)-2-pyridinecarbothioamide (I, R$_1$=CN, R$_2$=H)

Picolinic acid chloride was prepared by refluxing a solution of picolinic acid (20.0 g, 162 mmol) and thionyl chloride (24.0 mL, 325 mmol) in chloroform (200 mL) overnight. After excess thionyl chloride and chloroform was removed in vacuo, some of the acid chloride (15.0 g, 106 mmol) was added to a solution of 4-cyanoaniline (10.0 g, 84.6 mmol) and triethylamine (30.0 mL, 215 mmol) in methylene chloride (250 mL) at 0° C. under nitrogen. The reaction mixture was stirred at room temperature for 1 hour, poured into water (1 L), basified with 2.5N sodium hydroxide solution, and diluted with methylene chloride. The organic layer was dried over magnesium sulfate and concentrated to give a light brown solid (8.22 g, 36.9 mmol, 44%, mp 156°–159° C.).

Lawesson's reagent (11.84 g, 29.3 mmol) was added to a solution of the amide in anhydrous toluene (100 mL). The reaction mixture was refluxed for 3 hours and then preabsorbed onto silica gel. Flash chromatography (4 in diameter column, elution with 10% ethyl acetate in petroleum ether) afforded shiny orange crystals (4.35 g, 50%, mp 142°–144° C.).

$^1$H NMR (CDCl$_3$, 400 MHz): δ12.34 (br s, NH), 8.75 (d, J=8 Hz, 1H), 8.56 (d, J=4 Hz, 1H), 8.34 (d, J=9 Hz, 2H), 7.92 (t, of d, J=8 and 2 Hz, 1H), 7.74 (d, J=9 Hz, 2H), 7.52 (m, 1H).

IR (KBr, cm$^{-1}$): 3200, 2200, 1500.

MS (m/z): 239 (M+, 20), 206 (56), 122(23), 78(100).

Anal. Calcd. for C$_{13}$H$_9$N$_3$S: C, 65.25; H, 3.79; N, 17.56 Found: C, 64.92; H, 3.95; N, 17.17.

EXAMPLE 5

N-[3-[(1H-Imidazol-l-y)methyl]phenyl]-2-pyridinecarbothioamide Dihydrochloride Hydrate

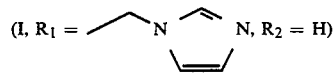

(I, R$_1$ = ...N...N, R$_2$ = H)

Step 1: Preparation of 3-[(1H-Imdiazol-l-yl)methyl]aniline

To a solution of 3-nitrobenzylbromide (15.0 g, 69 mmol) in dimethylformamide (100 mL), was added the sodium salt of imidazole (9.3 g, 103 mmol) under nitrogen. The reaction mixture was stirred at room temperature for 3 hours, poured into water (1 L), and extracted with ethyl acetate (3×500 mL). The organic layer was dried over magnesium sulfate and concentrated to give a dark brown solid. The crude material was recrystallized from ethyl acetate in petroleum ether to afford a pure tan solid (9.68 g, 47.7 mmol, 69%, mp 93°–95° C.). The nitro compound (18.7 g, 92.1 mmol) was reduced to the aniline compound by combining it with 10% palladium on carbon (0.6 g) in ethanol (300 mL) and treating it with 50 psi of hydrogen pressure in a Parr apparatus overnight. The reaction mixture was filtered through celite and concentrated to give a crude material (18.3 g). The pure aniline compound (7.55 g, 50%) was obtained by flash chromatography (6 in diameter column, elution with 90:5:2.5: CH$_2$Cl$_2$:MeOH:NH$_4$OH) as an oil.

¹H NMR (CDCl₃, 400 MHz): δ7.52 (s, 1H), 7.10 (t, J=8 Hz, 1H), 7.06 (s, 1H) 6.88 (s, 1H), 6.59 (d, of d, J=8 and 2 Hz, 1H), 6.53 (d, J=8 Hz, 1 H), 6.37 (br s, 1H), 4.99 (s, 2H), 3.22 (br s, NH₂).

MS (m/z): 173 (M+, 52), 123 (52), 106 (100), 94 (41), 91 (38).

Step 2: Preparation of N-[(1H-Imidazol-1-yl)methyl]phenyl]-2-pyridinecarboxamide Picolinic acid (5.80 g, 47.5 mmol) in dimethylformamide (150 mL) was reacted with 1,1'-carbonyldiimidazole (7.67 g, 47.3 mmol) for 0.5 hours. To this solution was added 3-[(1H-imidazol-1-yl)methyl]aniline (7.55 g, 43.6 mmol). The reaction mixture was stirred at room temperature for three days, poured into water (1.5 L), and extracted with ethyl acetate (3×500 mL). The organic layer was dried over magnesium sulfate, concentrated, and preadsorbed onto silica gel. Flash chromatography (4 in diameter column, elution with 2% methanol in methylene chloride) gave a pure ivory solid (6.8 g, 57%, mp 95°–97° C.).

¹H NMR (CDCl₃, 400 MHz): δ10.10 (br s, NH), 8.60 (d, J=5 Hz, 1H), 8.27 (d, J=8 Hz, 1H), 7.90 (t of d, J=8 and 2 Hz, 1H), 7.71 (s, 1H), 7.68 (d, J=8 Hz, 1H), 7.61 (s, 1H), 7.50–7.47 (m, 1H), 7.35 (t, J=8Hz, 1H), 7.10 (s, 1H), 6.94 (s, 1H), 6.90 (d, J=8 Hz, 1H), 5.14 (s, 2H).

IR (KBr, cm⁻¹): 3240, 1670.

MS (m/z): 278 (M+, 16), 200(100), 173(53), 172(47), 132(67), 104(56), 78(78),

Anal. Calcd. for C₁₆H₁₄N₄O: C, 69.05; H, 5.07; N, 20.13 Found: C, 69.30H, 5.45; N, 20.14.

Step 3: Preparation of N-[3-[(1H-Imidazol-1-yl)methyl]phenyl]-2-pyridinecarbothiamide Dihydrochloride Hydrate.

To a solution of N-[3-[(1H-imidazol-1-yl)methyl]phenyl]-2-pyridinecarboxamide (6.00 g, 21.5 mmol) in pyridine (150 mL), phosphorus pentasulfide (4.79 g, 10.8 mmol) was added under anhydrous conditions. The reaction mixture was refluxed for 4 hours, cooled to room temperature, poured onto ice (2 L), basified using 1N sodium hydroxide solution, and extracted with ethyl acetate (4×1 L). The organic layer was dried over magnesium sulfate and preabsorbed onto silica gel. Flash chromatography (4 in diameter column, elution with 30% 90:5:2.5 CH₂Cl₂:MeOH:NH₄OH in CH₂Cl₂) gave a pure orange oil. The oil was dissolved in ether and ethereal hydrogen chloride was added. The solid was filtered and recrystallized from methanol in ethyl acetate to give pure thioamide [2.8 g, 34%, mp 148°–150° C.(dec.)].

¹H NMR (CDCl₃, 400 MHz): δ12.33 (br s, NH), 9.35 (s, 1H), 8.67 (d, J=5 Hz, 1H), 8.49 (d, J=8 Hz, 1H), 8.05 (t of d, J=8 and 2 Hz, 1H), 7.95 (m, 2H), 7.82 (s, 1H), 7.72 (s, 1H), 768–7.65 (m, 1H), 7.49 (t, J=8 Hz, 1H), 7.36 (d, J=8 Hz, 1H), 5.50 (s, 2H)

IR (KBr, cm⁻¹): 3500, 1530.

MS (m/z): 294 (M+,6), 227(24), 226(100), 90(22), 89(24), 78(42), 69(28).

Anal. Calcd. for C₁₆H₁₈Cl₂N₄OS: C, 49.87; H, 4.71; N, 14.54 Found: C, 50.11; H, 4.65; N, 14.46.

EXAMPLE 8
N-[3-[(4-Morpholinyl)methyl]phenyl]-2-pyridinecarbothioamide

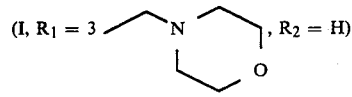

(I, R₁ = 3-morpholinylmethyl, R₂ = H)

Step 1: Preparation of 3-[(4-Morpholinyl)methyl]aniline

A reaction mixture containing 3-nitrobenzaldehyde (30 g, 200 mmol) and morpholine (34.9 mL, 400 mmol) in anhydrous methanol (150 mL) was prepared under nitrogen. After the solution was stirred for 15 minutes at 0° C., a 0.5M stock solution of zinc cyanoborohydride (400 mL, 200 mmol) was added. The ice bath was removed and the reaction mixture was stirred overnight. A white precipitate was removed by filtration and the filtrate was concentrated. The yellow residue was partitioned between methylene chloride (500 mL) and pH 7 buffer solution (500 mL). The organic layer was dried over magnesium sulfate and the volatiles were removed to give the crude product. The crude material was dissolved in ether and ethereal HCl was added to make the hydrochloride salt. The solid was collected, free-based using 1N sodium hydroxide solution, and extracted with ethyl acetate to give pure yellow crystals (25.16 g, 113 mmol, 55%, mp 45°–48° C.). The nitro compound was reduced to the aniline compound by combining it with 10% palladium on carbon (0.7 g) in ethanol (300 mL) and treating it with 50 psi hydrogen overnight. The reaction mixture was filtered through celite and concentrated to give a yellow oil (21.8 g. 100%).

¹H NMR (CDCl₃, 400 MHz): δ7.08 (t, J=8 Hz, 1H), 6.60 (m, 2 H), 6.57 (d, J=8 Hz, 1H), 3.70 (m, 6H), 3.40 (s, 2H), 2.43 (m, 4H).

MS (m/z): 192 (M+, 16), 107 (100), 106 (60).

Step 2: Preparation of N-[3-[(4-Morpholinyl)methyl]phenyl]-2-pyridinecarbothioamide Picolinic acid (13.9 g, 113 mmol) in dry dimethylforamide (250 mL) was reacted with 1,1'-carbonyldiimidazole (18.4 g, 113 mmol) for 0.5 hours. To this solution was added 3-[(4-morpholinyl)methyl]aniline (21.8 g, 113 mmol). After the solution had been stirred at room temperature for 6 days, it was poured into water (1.2 L) and extracted with ether (3×500 mL). The ether layer was washed with 1N sodium hydroxide solution (800 mL) and dried over magnesium sulfate. Ether was removed and the residue was adsorbed onto silica gel and flash chromatographed (6 in diameter column, elution with 3% methanol in methylene chloride) to give a pure orange oil (20.7 g, 70 mmol, 62%). The amide was treated with phosphorus pentasulfide (15.47 g, 34 mmol) in anhydrous pyridine (350 mL) at reflux temperature for 4.5 hours. The reaction mixture was poured onto ice (2 L), basified using 1N sodium hydroxide solution, and extracted with ether (4×500 mL). The ether layers were combined and dried over magnesium sulfate and concentrated. The residue was preabsorbed onto silica gel and flash chromatographed (4 in diameter column, elution with 2% methanol in methylene chloride) to yield a pure yellow solid (7.0 g, 32%, mp 90°–92° C.).

¹H NMR (CDCl₃, 400MHz): δ12.07 (br s, NH), 8.80 (d, J=8 Hz, 1H), 8.55 (d, J=5 Hz, 1H), 8.10 (d, J=7 Hz, 1H), 7.97 (s, 1H), 7.89 (t of d, J=8 and 2 Hz, 1H), 7.48 (m, 1H), 7.42 (t, J=7 Hz, 1H), 7.27 (d, J=7 Hz, 1H), 3.74 (m, 4H), 3.58 (s, 2H), 2.51 (br s, 4H).

IR (KBr, cm⁻¹): 3200, 1550.

MS (m/z): 313 (M⁺, 100), 228 (68), 226 (52), 194 (93).

Anal. Calcd. for $C_{17}H_{19}N_3OS$: C, 65.23; H, 6.12; N, 13.42 Found: C, 65.32; H, 6.08; N, 13.50.

The compounds N-[3-[(4-thiomorpholinyl)methyl]-phenyl]-2-pyridinecarbothioamide; and N-[3-[(4-methyl-1-piperazinyl)methyl]phenyl]-2-pyridinecarbothioamide dihydrochloride hemihydrate were prepared by the procedure of Example 8.

We claim:

1. The process for producing compounds of structural formula

[structure]

wherein R₁ =

[structures]

which comprises:

(a) reacting nitro aldehyde of structure

[structure (XI)]

with sodium borohydride to form the nitro alcohol of structure

[structure (XII)]

(b) reacting said nitro alcohol with stannous chloride dihydrate to afford the hydroxymethyl aniline of structure

[structure]

(c) reacting said hydroxymethyl aniline with two equivalents of the acid chloride derivative of (III) of structure

[structure]

to yield hydroxymethyl amide of structure

[structure (X)]

as well as amide ester of structure

[structure]

which can be converted to additional said hydroxymethyl amide with potassium carbonate in wet alcohol;

(d) reacting said hydroxymethyl amide with carbon tetrabromide and triphenylphosphine to afford the bromomethyl amide of structure

[structure]

(e) reacting said bromomethyl amide with heterocycles of structure

[structures]

or their sodium salts to yield basic amides of structure

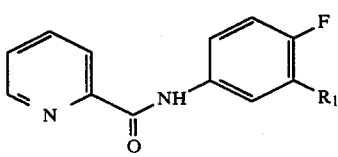
wherein $R_1$ is as defined above; and
(f) reacting said basic amides with phosphorus pentasulfide in pyridine to afford basic thioamides of structure.
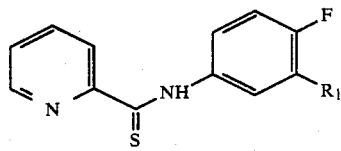
wherein $R_1$ is as defined above;
(g) and optionally treating said basic thioamides with hydrogen chloride to form the monoor dihydrochloride salt.
* * * * *